United States Patent [19]

Koprowski et al.

[11] 4,196,265

[45] Apr. 1, 1980

[54] METHOD OF PRODUCING ANTIBODIES

[75] Inventors: Hilary Koprowski, Wynnewood; Walter U. Gerhard; Carlo M. Croce, both of Philadelphia, all of Pa.

[73] Assignee: The Wistar Institute, Philadelphia, Pa.

[21] Appl. No.: 933,092

[22] Filed: Aug. 11, 1978

Related U.S. Application Data

[63] Continuation-in-part of Ser. No. 806,857, Jun. 15, 1977.

[51] Int. Cl.$^2$ .................. A01N 1/02; A61K 39/42
[52] U.S. Cl. ............................ 435/2; 424/85; 424/86
[58] Field of Search ............... 424/85, 86; 195/1.8

[56] References Cited

U.S. PATENT DOCUMENTS 2,768,114 10/1956 Koprowski et al. ............... 424/89

FOREIGN PATENT DOCUMENTS 1300391 12/1971 United Kingdom .

OTHER PUBLICATIONS

Gerhard & Koprowski, Nature, vol. 266, Mar. 4, 1977, pp. 360–361.
Milstein & Herzenberg, Immune System, "Genetics & Regulation," edited by Sercarz et al., (Academic Press), Dec. 1977, pp. 273–275.
Koprowski, Gerhard & Croce, Proc. Nat. Acad. of Sci. (USA), vol. 74, Jul. 1977, pp. 2985–2988.
Milstein & Kohler, "Antibodies in Human Diagnosis & Therapy", edited by Haber & Krause (Raven), Feb. 17, 1977, pp. 271–284.
The Lancet, editorial, Jun. 11, 1977, pp. 1242–1243.
Kohler, Pearson & Milstein, Somatic Cell Genetics, vol. 3, Feb. 7, 1977, pp. 303–312.
Kohler et al., Nature, vol. 256, (Aug. 7, 1975), pp. 495 to 497.
Kohler et al., Eur. J. Immunol., vol. 16, (1976), pp. 511–519.
Galfre et al., Nature, vol. 266, (Apr. 1977), pp. 550–552.
Welsh, Nature, vol. 266, (Apr. 1977), p. 495.

Primary Examiner—Sam Rosen

[57] ABSTRACT

Continuous cell lines of genetically stable fused cell hybrids capable of producing large amounts of monoclonal antibodies against specific viruses and their antigenic determinants have been developed. The cell lines are fused cell hybrids between viral antibody producing cells and myeloma cells. Fused cell hybrids between influenza virus-primed mouse spleen cells and mouse myeloma cells can be maintained indefinitely in culture and continue to produce large amounts of anti-influenza antibody.

18 Claims, No Drawings

METHOD OF PRODUCING ANTIBODIES

RELATED APPLICATIONS

This is a continuation-in-part of application Ser. No. 806,857, filed June 15, 1977.

BACKGROUND OF THE INVENTION

This invention relates to antibody culture and in particular the production of antibodies by living cells in vitro.

The production of antibodies specific for the antigenic determinants of viruses is of importance both for immunotherapy and for medical research.

Monoclonal antibodies for antigenic determinants of viruses have been produced in vitro in cultures of spleen cells infected with a virus. Up to now, however, production of antibody by spleen foci in culture declined after 30-40 days and ceased altogether after 90 days.

We have developed new techniques for producing antibodies, more particularly, the propogation of new cell lines which are genetically stable, can be cultivated and subcultivated indefinitely and produce large amounts of antibodies against viruses and their antigenic determinants. The new cell lines are fused cell hybrids of (a) myeloma cells, i.e., malignant cells from primary tumors of bone marrow, and (b) viral antibody producing cells preferably those of the spleen or lymph nodes of virus primed animals. A particularly preferred cell line is a fused cell hybrid between virus-primed mouse spleen cells and mouse myeloma cells. These cell lines can be maintained substantially indefinitely in a culture medium such as hypoxanthine-aminopterin-thymidine selected medium and continue to produce antibodies specific for the antigenic determinants of the virus. The cells can also be grown in vivo in a histocompatible animal to accumulate large amounts of antibodies in the serum and ascitic fluid of the animal.

Myeloma cells are themselves unique in that such cells are capable of producing antibodies albeit the specificity of these antibodies is as yet unknown. The particular species of animal from which the myeloma and spleen cells are derived is not critical insofar as it is possible to fuse the cells of one species with another, i.e., mouse to rat, rat to human. We prefer, however, to use the same species of animal as a source of both myeloma and viral antibody producing cells. Excellent results have been obtained with somatic cell hybrids between the viral antibody producing spleen cells of a BALB/c mouse previously immunized with a virus and myeloma cells of a BALB/c mouse. Particularly preferred myeloma cells are those of the MOPC-21 line called clone (P3×63 Ag8) and disclosed by Kohler et al in *Nature*, Vol. 256, 495-497 (1975).

Fused cell hybrids of BALB/c spleen cells and BALB/c myeloma cells have been previously described in the literature by Kohler et al in *Nature*, Vol. 256, 495-497 (1975) and *Eur. J. Immunol.*, Vol. 6, 511-519 (1976). These hybrids, however, were not derived from mice immunized with viruses, but rather from mice immunized with sheep red blood cells. Hybrids between sheep red blood antibody producing cells and myeloma cells are easily formed but the antibodies produced by the hybrids of Kohler et al are specific to sheep red blood cells and have no effect upon viruses. Prior to this invention, it was not known whether hybrids could be formed between viral antibody producing cells and myeloma cells.

Following is a procedure for preparing a cell line of hybrid cells by fusing the spleen cells of a BALB/c mouse previously immunized with influenza virus with myeloma cells of a BALB/c mouse. Although the procedure utilizes a particular strain of influenza virus, other viruses such as rabies, mumps, vaccinia, influenza strain 6-94, simian virus 40, polia, etc., can be used.

(A) PREPAATION OF SPLEEN CELLS FOR FUSION

In order to prepare the spleen cells for fusion, BALB/c mice, primed by an intraperitoneal injection of 1250 hemagglutinating units of purified influenza virus (A.PR/8/34 (HONI)) 2 to 3 months previously, received intravenously a booster dose of 100 hemagglutinating units of the homologous virus. The mice were sacrificed 7 days later and a spleen cell suspension was prepared in the manner taught by Gerhard et al, *Eur. J. Immunol.*, 5, 720-725 (1975). Red blood cells were lysed by incubation of 15 minutes at 4° C. in $NH_4Cl$ (0.83%). The resulting cell suspension was washed by one centrifugation (800×g) through heat-inactivated calf ser and one centrifugation in protein-free medium (RPM1 1640, buffered with 7.5 mM HEPES, pH 7.2).

(B) PREPARATION OF MYELOMA CELLS FOR FUSION

BALB/c (P3×63 Ag8) myeloma cells derived from the MOPC-21 line and deficient in HPRT (E.C.2.4.2.8) as described by Dr. Cesar Milstein in *Nature*, Vol. 256, 495-497 (1975), were maintained in Engle's minimal essential medium (MEM) containing 10% fetal calf and 10% horse serum. The growth of P3×63 Ag8 myeloma cells is inhibited by selective hypoxanthine-aminopterin-thymidine medium.

(C) PRODUCTION OF HYBRIDS

Production of hybrids was accomplished by mixing ten million BALB/c (P3×63 Ag8) myeloma cells with $10^8$ spleen cells obtained from the virus infected BALB/c mice. The cell mixture was centrifuged at 800×g and the cells were resuspended for fusion in a 50% solution (w/v) of polyethylene glycol-1000 (PEG) diluted in minimum essential medium (MEM) without serum. Following fusion procedures taught by Davidson et al, *Somat, Cell Genet.* 2, 175-176, the polyethylene glycol was diluted first with MEM without serum and then with serum before the cells were seeded in five 75-cm Falcon flasks in hypoxanthine-aminopterin-thymidine (HAT) selective medium. The cultures were incubated at 37° C. in an atmosphere of 95% air/5% $CO_2$, and every 7 to 10 days the culture medium was partially replaced by fresh HAT medium (¼ to ½).

Ten to fifteen days after incubation of cultures produced by fusion of spleen cells of PR8 immunized mice with P3×63 Ag8 cells, cell growth was observed in one flask. All growth in HAT medium is indicative of successful hybridization between mouse spleen and mouse myeloma cells. These cells, referred to as HK-PEG-1, were propagated continuously in HAT medium and were cloned in microplates (Linbro) at limiting dilution. The other 4 flasks, none of which showed cell growth, were discarded 3 weeks after fusion. A deposit of the cell line culture identified as HK-PEG-1 is on deposit with the American Type Culture Collection and is assigned the accession number ATCC CL 189.

(D) KARYOLOGICAL ANALYSIS

As shown in Table 1, the P3×63 Ag8 parental cells contained an average of 63 chromosomes and BALB/c spleen cells of 40 chromosomes. Thus, the 92 chromosomes in the HK-PEG-1 cells represented approximately the sum of chromosomes of 2 parental cells. The kuryology of the hybrid clone HK-PEG-1 and of subclones was monitored for 4 months with no significant change in the karyotype.

TABLE 1

| Number of Chromosomes in Parental and Hybrid Cells | |
|---|---|
| Cells | Average Number of Chromosomes per Cell |
| P3 × 63 Ag8 | 63* |
| BALB/c spleen cells | 40 |
| H5-PEG-1 | 92* |

*Including 2 metacentric marker chromosomes.

(E) ANALYSIS OF THE IMMUNOGLOBIN PRODUCED BY THE HYBRID CELLS

Culture fluids of HK-PEG-1 and P3×63 Ag8 cells were analyzed for the presence of immunoglobulins (ig) reacting in the radioimmune assay (RIA) with PR8. P3×63 Ag8 is known to secrete IgG1, k. As shown in Table 2, P3×63 Ag8 cuture fluids did not contain Ig with anti-PR8 reactivity. In contrast, large quantities of IgG anti-PR8 antibodies were produced by HK-PEG-1.

TABLE 2

| Class of Anti-PR8 Antibody Produced by HK-PEG-1 Cultures | | | | |
|---|---|---|---|---|
| Culture Fluid | CPM Observed in RIA with Antisera Labeled with 125$_I$ | | | |
| Assayed in RIA* | Anti-F(ab')$_2$ | Anti-IgM | Anti-IgA | Anti-IgG |
| P3 × 63 Ag8 | 44 ± 24** | ND** | ND | 185 |
| HK-PEG-1 | 4255 ± 158** | 204 | 26 | 8335 |

*Medium from cultures with similar cell concentration. Analysis performed on replicate samples of 15 ul (P3 × 63 Ag8) or 7.5 ul (HK-PEG-1) of culture fluid.
**Mean + SE of 6 determinationes. Other entries: mean of RIA done in duplicate.
***ND = Not Determined.

The data of Table 3 indicate that the viral antibodies (anti-PR) produced by the hybrid cells are specific for the antigen (hemagglutinin) of the PR8. This is evident from the functional assays in which the antibodies (roughly 40 ug/ml) exhibited a hemagglutinin inhibition (HI) but no detectable neuraminidase inhibition (NI).

TABLE 3

| Activity of Antibody Produced by HK-PEG-1 in Functional Assays Against PR, Virus | | |
|---|---|---|
| Antibody secreted in vitro by | HI-titer* | NI-titer* |
| HK-PEG-1 and concentrated by ammonium sulfate precipitation** | (log 10) 2.98 | (log 10) *1.00 |

*Hemagglutination inhibition (HI) and neuraminidase inhibition (NI) against PR8 virus.
**Fifty ml of HK-PEG-1 culture medium was precipitated with ammonium sulfate at 4° C. at 42% (v/v) saturation. Precipitate was dialyzed against PBS and concentrated by ultrafiltration to 0.6 ml. This final sample contained, as determined by RIA, 47% of the antiviral antibody present in the starting volume of culture medium and thus represents roughly a 40-fold concentration of antiviral antibodies.

(F) CLONAL ORIGIN OF THE HYBRID CELLS

The clonal origin of HK-PEG-1 was tested by 3 independent criteria:

(i) Concentraged Ig obtained from HK-PEG-1 mass cultures (see legend, Table 3) was subjected to isoelectric focusing, anti-PR8 antibodies with IgG1 heavy chain determinant(s) accumulated in a restricted pH range.

(ii) The antibody was tested in the RIA for its cross-reactivity against various viruses known to be antigenically related to PR8 and was found to be specific for a determinant of the hemagglutinin (HA) of PR8. However, 20% to 25% of splenci PR8-primed precursor B cells exhibit this strain-specific anti-HA (PR8) reactivity. Taken alone, the antibody reactivity is, therefore, a rather weak criterion for determining monoclonality of HK-PEG-1.

(iii) In order to exclude the possibility that cells productin antiviral antibody constituted only a small fraction of the hybrid cell population, culture fluids derived from 12 clones of HK-PEG-1 hybrid line were assayed for the presence of anti-PR8 antibody and its specificity. As shown in Table 4, 11 of the 12 clones produced anti-PR8 antibody. Furthermore, these antibodies were specific for a determinant of the HA of the PR8 virus.

TABLE 4

| Anti-PR8 Antibody Produced by Clones of HK-PEG-1 Cultures | |
|---|---|
| Culture Fluid from HK-PEG-1 Clone # | Concentration of Anti-PR8 HA Antibody* (ug/ml) |
| 2 | 2 |
| 3 | 1.2 |
| 5 | 2.4 |
| 6 | 3.4 |
| 7 | 4.7 |
| 9 | 6.9 |
| 10 | 4.7 |
| 11 | 5.8 |
| 12 | *0.02 |
| 13 | 2.8 |
| 14a | 2.7 |
| 14b | 2.6 |

*Quantitation based on RIA done with $^{125}$I-anti-F(ab')$_2$.

(G) TUMORIGENICITY OF THE HYBRID CELLS

In order to determine the tumorigenicity of the hybrid cells, adult BALB/c mice were injected subcutaneously in the abdominal wall with either HK-PEG-1 (1×10$^7$) or P3×63 Ag8 (1×10$^7$) cells.

As shown in Table 5, ten to twelve days after implantation, tumors developed at the site of inoculation of 5/5 mice injected with the HK-PEG-1 cells and in 3/5 mice injected with the parental P3×63 Ag8 cells. In a second experiment, 4/5 mice developed tumors after inoculation with hybrid cells and 3/5 after inoculation with P3×63 Ag8 cells. After i.p. injection of cells (experiment 3, Table 5), tumors were found to grow as masses in the peritoneal cavity. In order to produce ascitic fluid, it was necessary to inject the mice with tumor cells resuspended in complete Freund adjuvant. In a fourth experiment, pristane-primed mice developed ascites after i.p. inoculation of cells of the HK-PEG-1 clones.

TABLE 5

| Exp. No. | Route of Inoculation | Inoculum | Ratio of Mice Developing: | |
|---|---|---|---|---|
| | | | Subcutaneous Tumor | Ascites |
| 1 | subcutaneous | HK-PEG-1 | 5/5 | —* |
| | | P3 × 63 Ag8 | 3/5 | — |
| 2 | subcutaneous | HK-PEG-1 | 4/5 | — |
| | | P3 × 63 Ag8 | 3/5 | — |

TABLE 5-continued

| Exp. No. | Route of Inoculation | Inoculum | Ratio of Mice Developing: Subcutaneous Tumor | Ascites |
|---|---|---|---|---|
| 3 | intraperitoneal | HK-PEG-1 in CFA | — | 3/3 |
|  |  | HK-PEG-1 | — | 0/3 |
| 4 | intraperitoneal** | HK-PEG-1 cl 6 | — | 4/4 |
|  |  | HK-PEG-1 cl 7 | — | 4/4 |
|  |  | HK-PEG-1 cl 12 | — | 4/4 |

*No tumor or ascites developed 30 days after inoculation.
**Pristane-primed mice.

The results of these studies indicate that hybrid cells between mouse myeloma and normal spleen cells behave as the malignant parent without suppression of malignancy.

Sera and ascitic fluid obtained from tumor-bearing mice at various intervals after injection were tested to determine the concentration of anti-PR8 antibody by means of the RIa. The results are shown in Table 6.

TABLE 6

Anti-PR8 Antibodies in Sera and Ascitic Fluids Obtained From Mice Injected with HK-PEG-1 Cells

| Exp. No. | Material Obtained Days After Injection | Type of Material | Estimated Concentration of Antiviral Antibody* mg/ml |
|---|---|---|---|
| 1 | 28 | Serum | 1.35 |
|  |  | Serum | 1.1 |
|  |  | Serum | 2.3 |
| 2 | 19 | Serum | 0.9 |
|  |  | Serum | 1.6 |
|  |  | Serum** | 1.2 |
|  |  | Ascites** cl 6 | 0.5 |
|  |  | Ascites cl 7 | 0.45 |
|  |  | Ascites cl 12 | 0.002 |

Quantitation based on RIA done with $^{125}$I-anti-F(ab')$_2$.
**From the same mouse.

Sera of mice injected subcutaneously with HK-PEG-1 cells (experiments 1 and 2) contained anti-PR8 antibodies at a concentration of 1 to 3 mg/ml. Anti-PR8 antibodies were also found in the ascitic fluid of mice injected i.p. (experiment 4) with hybrid cells, although the concentration of antibodies was 3- to 4-fold lower than in the serum.

Electrophoresis of serum obtained from mice bearing HK-PEG-1 tumors revealed the presence of 3 main Ig-populations: one corresponding to the parental (P3×63 Ag8) IgG1; one characteristic of IgG3; and a third intermediate between the other two. In order to determine with which class of immunoglobulins the antiviral antibody was associated, ascitic fluid was collected from 20 pristane-primed mice was pooled and the immunoglobulins separated therefrom. Separation was accomplished by using a technique as follows:

Ascitic fluid collected from the mice was pooled and the pool neutralized with phosphate-buffered saline (PBS). An equal volume of saturated ammonium sulfate was added at 4° C., and the precipitated protein was dissolved in PBS and dialyzed against 0.01 M Tris buffer at pH 8.0. The precipitate, formed after overnight dialysis, was redissolved in PBS and reprecipitated by dialysis against 0.01 M Tris buffer at pH 8.0 The supernatant from the original dialysate was absorbed on DE-52 (Whatman) column equilibrated with 0.01 M Tris buffer, pH 8.0, and eluted using a linear NaCl gradient (0.05 to 0.15 M NaCl in 0.01 M Tris, pH 8.0).

Following precipitation of the IgG3 by dialysis against 0.01 M Tris buffer, the remaining supernatant was found, by electrophoresis, to lack one of the components seen i the ascites pool prior to fractionation. Chromatography of this material on DE-52 did not result in complete resolution of the remaining components, but electrophoresis of the individual aliquots indicated the presence of two major components: one corresponding to the parental (P3×63 Ag8) IgG1, and the other indicative of a hybrid Ig, intermediate between IgG1 and IgG3, which was also observed i the serum of HK-PEG-1 tumor-bearing mice (see above).

The concentration of anti-PR8 antibody was determined in the RIA using $^{125}$I-anti-F(ab')$_2$ and the specific anti-PR8 activity was computed as ratio of anti-PR8 (mg/ml)$^2$Ig (mg/ml), the latter estimate being based on the OD 280 measurement assuming absorptivity (1%, 1 cm) for mouse Ig of 14.0. The specific anti-PR8 activity determined in the low salt precipitate, was roughly 2 times higher than at the peak of the anti-PR8 activity of the DE-52 chromatography (0.06 in fraction 21). Analysis of the samples in the RIA with $^{123}$I-anti-IgG1 indicated that approximately 15% of the anti-PR8 antibodies in the low salt precipitate expressed G1 determinants. In contrast, $^{125}$I-anti-F(ab')$_2$ was as effective in quantitating the anti-PR8 antibodies in the various fractions of the DE-52 chromatography.

Another series of tests were performed with rabies virus.

BALB/c mice were primed with vaccine containing inactivated rabies virus (ERA strain) and one month later received an intravenous booster inoculation of the same vaccine. The mice were sacrificed three days after the booster and hybrid cells were formed by fusion of the spleen cells with P3×63 Ag8 myeloma cells as described earlier. A large number of the hybrid cells produced anti rabies virus antibodies. In contrast, when mice were sacrificed ten days after the booster the number of hybrid cells producing anti rabies antibodies was quite low. This procedure was employed to obtain the hybridomas employed for the tests shown in Tables 7, 8 and 9.

The strains of rabies virus employed in the following tests are known strains in the art. For example, strain ERA is described, inter alia, in U.S. Pat. Nos. 3,423,505 and 3,585,266. HEP-Flury is described, inter alia, in U.S. Pat. No. 2,768,114 and SAD is described in Can. J. of Microbiology, 6, 606 (1960). Similarly the analyticl tests employed are well known in the art.

Fifty-two hybridomas that produced anti rabies virus antibodies as determined by radioimmune assay (RIA) were tested against three different stains of rabies virus (ERA, CVS and HEP - Flury strains). Moreover, four different assays were used, Virus Neutralization (VN), Cytotoxic Test (CT), Membrane Fluorescence (M), and Nucleocapsid Fluorescence (NC). The results of the tests are shown in Table 7.

TABLE 7

| Number of Hybridomas | Reactivity Against Virus Strains in Different Assays: ERA VN | ERA CT | ERA M | ERA NC | CVS VN | CVS CT | CVS M | CVS NC | HEP VN | HEP CT | HEP M | HEP NC |
|---|---|---|---|---|---|---|---|---|---|---|---|---|
| 7 | + | + | + | − | + | + | + | − | + | + | + | − |
| 2 | + | + | + | − | ± | ± | + | − | + | + | + | − |
| 2 | + | + | + | − | + | + | + | − | − | − | − | − |
| 11 | + | + | + | − | − | − | − | − | + | + | + | − |
| 2 | + | + | + | + | − | − | − | + | + | + | + | + |
| 2 | + | + | + | + | − | − | − | + | − | − | − | + |
| 1 | + | + | + | − | − | − | − | − | − | − | − | − |
| 2 | − | ± | + | + | − | − | − | + | + | + | + | + |
| 1 | − | − | − | − | − | − | − | − | + | + | + | − |
| 22 | − | − | − | + | − | − | − | + | − | − | − | + |

As Table 7 demonstrates, antibodies that reacted with one strain may not interact with another strain of rabies virus. As shown in Table 7, of 52 hybrid cells secreting rabies antibodies, nine reacted in virus-neutralization, cytotoxicity and membrane immunofluorescence assays with all three strains of rabies, ERA, CVS and HEP-Flury; fifteen reacted with the ERA and HEP strains; two with ERA and CVS; three with ERA only and one with HEP virus only. Twenty-eight hybrid cultures produced antibodies reacting with nucleocapsids of all 3 virus strains; and of those 23 reacted only with nucleocapsids and with no other viral components.

Analysis of antigenic relationship among strains of street and fixed strains of rabies virus was studied using additional ten strains of different geographical origin. The hybridomas were produced as described above using ERA. Results presented in Table 8 indicate that fixed strain Kelev virus is neutralized only by antibodies secreted by one hybridoma (No. 120) and the recently discovered South African street virus (Duvenhage) only by antibodies secreted by two hybridomas. In contrast, all street virus strains seem to be cross-reactive in VN except for the AF strain which did not seem to react with the antibody of No. 193. Hybridoma antibodies were found to be quite heterogenous in VN assays with fixed strains of virus. For instance, the PM and CVS strains, which were both derived from the Pasteur strain, reacted differently from the Pasteur strain and from each other. Conversely, the SAD virus and its derivative ERA reacted in an identical fashion with antibodies secreted by the same hybridomas. Finally, the non-virulent HEP was found to be cross-reactive with the Kelev strain in the VN with No. 120 antibodies. In addition, however, HEP was neutralized by antibodies secreted by three other hybridomas.

Table 8

Cross-reactivity between strains of rabies virus of various origins determined in neutralization test with hybridoma antibody

| | Origin of Strain: Host | Country | Prototype | Derivative | Neutralization Index (by Logs): 101 | 110 | 194 | 120 | 103 | 193 | 104 |
|---|---|---|---|---|---|---|---|---|---|---|---|
| | | | SAD | | > 3.0 | > 3.0 | 33 > 3.0 | 2.5 | 3.0 | 1.5 | 0 |
| | Dog | USA | | ERA | > 3.0 | 3.0 | > 3.0 | 2.5 | 3.0 | 1.0 | 0 |
| | | | Pasteur | | > 3.0 | > 3.0 | > 3.0 | 1.0 | 3.0 | 1.0 | 0 |
| Fixed | Cow | France | | PM | 0 | > 3.0 | > 3.0 | 3.0 | 3.0 | 0 | 0 |
| | | | | CVS | > 3.0 | 2.0 | > 3.0 | 0 | 0 | 0 | 0 |
| | Man | USA | HEP Flury | | > 3.0 | > 3.0 | 0 | 2.0 | 3.0 | 0 | 0 |
| | Dog | Israel | Kelev | | 0 | 0 | 0 | > 3.0 | 0 | 0 | 0 |
| | Dog | USA | NYC | | > 3.0 | 3.0 | 3.0 | 2.0 | 3.0 | 1.0 | 0 |
| | Bat | USA | UD | | 1.5 | > 3.0 | > 3.0 | 2.0 | > 3.0 | 1.5 | 0 |
| | | Brazil | DR | | > 2.0 | 1.5 | > 2.0 | 1.5 | 1.0 | 1.0 | 0 |
| Street | Fox | France | AF | | 2.0 | 2.0 | > 2.0 | 2.0 | 2.0 | 0 | 0 |
| | Dog | Rwanda | RD | | > 3.0 | > 3.0 | > 3.0 | 2.5 | > 3.0 | 2.5 | 0 |
| | Man | South Africa | Duvenhage | | 0 | 0 | 1.5 | 1.5 | 0 | 0 | 0 |

Note: Intracytoplasmic fluorescence following staining in the presence of medium from hybridoma 104

Cells infected with all viruses regardless of origin showed intracytoplasmic fluorescence after fixation and exposure to antibodies produced by hybridoma 104 (NC assay), even though none of the viruses reacted with the same hybridoma in VN. This confirms that although the hybridomas antibodies easily distinguish strains of fixed rabies virus in VN, CT and MF tests, the antibodies react with all strains of rabies in the NC assay.

The results shown in Tables 7 and 8 demonstrate that the anti rabies virus antibody producing hybrid cells are very useful for research and analytical purposes.

Hybrid cultures secreting rabies virus-neutralizing antibodies protect mice against the lethal effect of rabies virus. Cells of hybridoma mass cultures C-1 and B-1 and of clone 110-5 (see Table 9) were emplanted subcutaneously into BALB/c mice. Serum obtained from these mice within 2 weeks after implantation of the C-1 and 110-5 hybridomas showed a hundredfold higher concentration of rabies antibodies than medium from tissue cultures of the same hybridoma. Five days after implantation of hybridomas, mice were challenged intracerebrally with a lethal doze of PM rabies virus. As shown in Table 9, mice that were implanted with hybridoma cultures that secreted VN antibody survived viral challenge, whereas mice that carried hybridomas that did not secrete VN antibody were not protected.

Table 9

Protection of mice against challenge by rabies virus by hybridoma antibodies

| Hybri-doma | Number of Cells Inoculated | VN | Number of Mice Protected/Number Challenged |
|---|---|---|---|
| C-1 | $5 \times 10^6$ | + | 6/6 |
| 110-5 | $5 \times 10^5$ | + | 9/10 |
|  | $5 \times 10^4$ | + | 6/6 |
| B-1 | $5 \times 10^6$ | − | 0/6 |
| — | none | − | 0/6 |

The cell line of this invention represents a hybrid culture displaying characteristics of both the normal spleen and the myeloma parental cells and appears to be derived from a single fusion event. The cells are hybrid in nature because:

(a) The cell line has been grown for several months in selective HAT medium which inhibits the growth of the parental P3×63 Ag8 myeloma cells but not of the normal spleen cells which, in turn, would probably not survive for more than 4 to 5 weeks in vitro;

(b) The number of chromosomes in the hybrid cells is close to the sum of that of the normal mouse and myeloma parent cells;

(c) The HK-PEG-1 hybrid produces not only IgG1, which is also secreted by P3×63 Ag8, but IgG3 as well, and probably, hybrid molecules; and (d) The hybrid produces antibodies with antiviral activity, whereas P3×63 Ag8 does not.

Although the antibodies are best produced by propogating the hybrid cell lines in vitro, antibodies can also be produced by injecting a histocompatible animal with the hybrid cell line and producing the antibodies in vivo. For example, mice, relatively inexpensive animals, may be injected with the mouse derived antibody producing cells of this invention to produce recoverable antibodies in the sera and ascitic fluids. Table 6, discussed previously, shows the amount of antibody obtained under such conditions.

The antibodies produced by the hybrids can be harvested using standard techniques and may be used in analytical medical research for identification of viral antigens in blood samples and culture mediums. Those antibodies produced in vitro are homogeneous and highly specific to the viral antigen. A supply of various homogeneous antibodies, each highly specific to a particular antigen permits researchers to rapidly determine the specificity of an antigen and/or characterize viral antigens. In addition, the antibodies can be administered to diseased animals to assist in combating the disease.

We claim:

1. A process for producing viral antibodies comprising fusing a viral antibody producing cell and a myeloma cell to provide a fused cell hybrid, culturing said hybrid and collecting the viral antibodies.

2. The process of claim 1 wherein said hybrid is cultured in vitro.

3. The process of claim 2 wherein said hybrid is cloned and cultured in a medium containing hypoxanthine-aminopterin-thymidine.

4. The process of claim 1 wherein said hybrid is injected into a histocompatible animal and cultured in vivo.

5. The process of claim 1 wherein said viral antibody producing cell is a cell selected from the group consisting of spleen cells and lymph node cells.

6. The process of claim 5 wherein said spleen is mouse spleen and said myeloma is mouse myeloma.

7. The process of claim 5 wherein the said mouse is a BALB/c mouse.

8. The process of claim 6 wherein said myeloma is (P3 63 Ag8) derived from the MOPC-21 line.

9. The process of claim 1 wherein said viral antibody producing cell is obtained from an animal immunized with a virus.

10. The process of claim 1 wherein said viral antibody producing cell is obtained from a mouse immunized with a virus.

11. The process of claim 1 wherein said viral antibody producing cell is obtained from an aminal immunized with an influneza virus.

12. The process of claim 1 wherein said viral antibody producing cell is obtained from an animal immunized with a rabies virus.

13. A process for producing antibodies comprising injecting a BALB/c mouse with a virus to induce antibody formation of spleen cells of said mouse, forming a fused cell hybrid of said viral antibody producing splenic cells with a BALB/c myeloma cell clone (P3×63 Ag8) derived from the MOPC-21 line, culturing said hybrid in vitro in selective HAT medium and harvesting the antibodies produced.

14. The process of claim 13 wherein said virus is an influenza virus.

15. The process of claim 13 wherin said virus is simian virus 40.

16. The process of claim 13 wherein said virus is a rabies virus.

17. A composition comprising a continuous cell line which produces influenza antibodies in vitro in hypoxanthine-aminopterin-thymidine medium comprising a fused cell hybrid of influenza primed BALB/c mouse spleen and MOPC-21 mouse myeloma and a culture medium therefor.

18. The composition of claim 17 wherein said continuous cell consists essentially of clone HK-PEG-1.

* * * * *

UNITED STATES PATENT AND TRADEMARK OFFICE
CERTIFICATE OF CORRECTION

PATENT NO. : 4,196,265
DATED : April 1, 1980
INVENTOR(S) : Hilary Koprowski, Walter U. Gerhard & Carlo M. Croce It is certified that error appears in the above—identified patent and that said Letters Patent is hereby corrected as shown below:

Column 1, immediately below the Title, add the following

— The invention described herein was made in the course of work under a grant or award from The Department of Health, Education and Welfare —

Signed and Sealed this

Twenty-first Day of October 1980

[SEAL]

Attest:

SIDNEY A. DIAMOND

Attesting Officer

Commissioner of Patents and Trademarks